United States Patent
Kobayashi

(10) Patent No.: US 8,279,998 B2
(45) Date of Patent: Oct. 2, 2012

(54) X-RAY IMAGE FORMATION DEVICE

(75) Inventor: Masaki Kobayashi, Oume (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 0 days.

(21) Appl. No.: 13/057,063

(22) PCT Filed: Aug. 12, 2009

(86) PCT No.: PCT/JP2009/064258
§ 371 (c)(1),
(2), (4) Date: Feb. 1, 2011

(87) PCT Pub. No.: WO2010/024125
PCT Pub. Date: Mar. 4, 2010

(65) Prior Publication Data
US 2011/0129059 A1 Jun. 2, 2011

(30) Foreign Application Priority Data
Aug. 26, 2008 (JP) .................... 2008-216811

(51) Int. Cl.
*A61B 6/00* (2006.01)
(52) U.S. Cl. ............................................ 378/8
(58) Field of Classification Search .............. 378/8
See application file for complete search history.

(56) References Cited

U.S. PATENT DOCUMENTS

| | | | |
|---|---|---|---|
| 5,751,782 A | 5/1998 | Yoshitome | |
| 6,504,893 B1 * | 1/2003 | Flohr et al. | 378/8 |
| 6,639,965 B1 * | 10/2003 | Hsieh et al. | 378/8 |
| 6,650,726 B2 | 11/2003 | Sembritzki et al. | |
| 2002/0025017 A1 * | 2/2002 | Stergiopoulos et al. | 378/8 |
| 2002/0172321 A1 | 11/2002 | Sembritzki et al. | |
| 2006/0056578 A1 * | 3/2006 | Rubin et al. | 378/4 |
| 2007/0140535 A1 * | 6/2007 | Li et al. | 382/128 |
| 2007/0183639 A1 * | 8/2007 | Kohler et al. | 382/131 |

FOREIGN PATENT DOCUMENTS

| | | |
|---|---|---|
| JP | 61-259647 A | 11/1986 |
| JP | 2-006530 B2 | 2/1990 |
| JP | 9-024045 A | 1/1997 |
| JP | 2000-139892 A | 5/2000 |
| JP | 2002-360560 A | 12/2002 |
| JP | 2006-311941 A | 11/2006 |

OTHER PUBLICATIONS

International Search Report of PCT/JP2009/064258, mailing date Nov. 17, 2009.

* cited by examiner

*Primary Examiner* — Alexander H Taningco
(74) *Attorney, Agent, or Firm* — Westerman, Hattori, Daniels & Adrian, LLP

(57) ABSTRACT

CT imaging is performed twice (S1101), which is set as the normal number of rotations, and a sinogram is corrected (S1102) based on the sinogram obtained by performing CT imaging twice. Since the cycles of data variation caused by respiration are controlled so as not to overlap one another, usually the data variations caused by respiration are eliminated by performing CT imaging twice. However, depending on irregularity in the respiration cycle of the subject, data variation components sometimes overlap at the same angle in spite of the fact that the cycles of data variation caused by respiration are controlled so as not to overlap one another. Therefore, when data variation components remain overlapped at the same angle, CT imaging is performed one additional time (S1104) and the sinogram is corrected (S1102) using the sinogram obtained by performing the additional CT imaging.

11 Claims, 11 Drawing Sheets

X-RAY IMAGE FORMATION DEVICE

TECHNICAL FIELD

The present invention relates to an X-ray image formation device such as an X-ray CT device.

BACKGROUND ART

A typical X-ray CT device comprises an X-ray generator and an X-ray detector which are placed opposing each other with a subject therebetween, and realizes CT imaging by executing radiation and detection of X-rays while rotating the X-ray generator and the X-ray detector relative to the subject. Projection data indicating a degree of X-ray attenuation (degree of X-ray absorption by the subject) are collected for each rotational angle during the CT imaging, and a tomographic image (CT image) of the subject is formed based on the projection data obtained at a plurality of rotational angles.

During the process of CT imaging, if the imaging target site such as an organ moves due to a body movement of the subject such as the respiratory movement, artifacts or the like may arise in the CT image that is finally obtained. In consideration of this, in the related art, there is proposed a respiration synchronization scan or the like in which the respiratory movement of the subject is detected and the CT imaging (scan) is executed to match a phase which can be assumed to have no movement or the like of the organ due to respiration (refer to Patent Literature 1 and 2).

RELATED ART REFERENCES

Patent Literature

Patent Literature 1: JP 2000-139892 A
Patent Literature 2: JP 2006-311941 A

DISCLOSURE OF INVENTION

Problem to be Solved

In the technique of the respiration synchronization scan described above, however, a dedicated detection device for detecting the body movement, such as a respiration detection device, is required. As a result, the overall diagnostic system including the X-ray CT device has suffered problems such as an increase in cost and an increase in structural complexity. In addition, such a respiration detection device must be attached to and detached from the subject as needed, resulting in extra work. Moreover, there has also been a problem in that the reliability of the tomographic image may be reduced when the respiration detection device mounted on the subject is drawn in the tomographic image.

Under these circumstances, the present inventors have researched and developed a technique for improving quality of an image obtained by the X-ray image formation device such as the X-ray CT device, and have noted a technique for forming an image while reducing the influence of a periodical body movement of the subject.

The present invention has been conceived in the course of research and development, and an advantage of the present invention is that image quality of an image of a subject formed using X-rays is improved by reducing influence due to the periodic body movement of the subject.

Means for Solving the Problem

In order to realize the above-described advantage, according to one aspect of the present invention, there is provided an X-ray image formation device comprising an X-ray measurement unit which obtains X-ray detection data by radiating X-rays to a subject in a manner to circle around the subject and detecting the X-rays, a body movement measurement unit which obtains body movement period data related to a periodic body movement of the subject, a circling controller which controls the circling of the X-rays by the X-ray measurement unit based on the body movement period data such that a body movement periodic component in the X-ray detection data obtained for each round of circling is shifted in the X-ray detection data for a plurality of rounds of circling, and an image formation unit which forms image data of the subject while correcting the body movement periodic component based on the X-ray detection data obtained by the plurality of rounds of circling, wherein the circling controller executes a control to add another round of circling of the X-rays when the body movement periodic components overlapped with each other remain in the X-ray detection data obtained by a normal number of rounds of circling which is set in advance.

In the above-described configuration, the circling of the X-ray may be relative between the subject and the X-ray. For example, the subject may be fixed at the center of the circling with respect to the device of the above-described configuration and the X-rays radiated through the center of circling rotated, or, alternatively, the X-rays radiated through the center of circling may be fixed with respect to the device of the above-described configuration and the subject rotated about the center of the circling. Alternatively, the relative circling may be realized by rotating both the subject and the X-rays. In addition, each round of circling is realized, for example, by a relative rotation of 180 degrees between the subject and the X-rays, but alternatively, each round may be realized, for example, by a relative rotation of 360 degrees between the subject and the X-rays. With the above-described configuration, the image data of the subject can be formed while correcting for the body movement periodic component related to the periodic body movement of the subject.

According to another aspect of the present invention, preferably, in the X-ray image formation device, the body movement measurement unit obtains the body movement period data based on a body movement periodic component related to a periodic body movement of the subject included in the X-ray detection data.

According to another aspect of the present invention, preferably, in the X-ray image formation device, the body movement measurement unit extracts the body movement periodic component from a sinogram correlating an angle of circling and X-ray projection data for each round of circling.

According to another aspect of the present invention, preferably, in the X-ray image formation device, the circling controller controls the circling of the X-rays by the X-ray measurement unit such that the body movement periodic component appearing in the sinogram obtained for each round of circling does not overlap on the same angle in the sinograms for a plurality of rounds of circling.

According to another aspect of the present invention, preferably, in the X-ray image formation device, the circling controller determines a start timing of circling of the X-rays based on a period of body movement calculated from body movement period data such that a phase of the body movement periodic component appearing in the sonogram obtained for each round of circling is shifted in the sinograms for the plurality of rounds of circling.

According to another aspect of the present invention, preferably, in the X-ray image formation device, the circling controller executes a control such that, when a bodymovement periodic component overlapping on a same angle remains in the sinogram obtained by the normal number of rounds of circling, the body movement periodic component is shifted from the angle in the sinogram obtained by adding another round of X-rays.

According to another aspect of the present invention, preferably, in the X-ray image formation device, the image formation unit forms the image data of the subject based on the sinograms obtained by a plurality of rounds of circling while correcting projection data of an angle where the bodymovement periodic component appears in a sinogram of one round of circling using projection data corresponding to the angle in a sinogram of another round of circling.

In order to achieve the advantage described above, according to another aspect of the present invention, there is provided a program for controlling an X-ray measurement unit which obtains X-ray detection data by radiating X-rays to a subject in a manner to circle around the subject and detecting the X-rays, the program causing a computer to realize a body movement measurement function in which body movement period data related to a periodic body movement of the subject is obtained, and a circling control function in which the circling of the X-rays by the X-ray measurement unit is controlled based on the body movement period data such that a body movement periodic component in the X-ray detection data obtained for each round of circling is shifted in the X-ray detection data for a plurality of rounds of circling, and another round of circling of the X-rays is added when the body movement periodic components overlapped with each other remain in the X-ray detection data obtained by a normal number of rounds of circling which is set in advance.

The program may be stored, for example, in a recording medium such as a disk or a memory and read into a computer through the recording medium, or, alternatively, the program may be provided to the computer through a network or the like. The computer includes, for example, general computers which are commercially available, and also devices having hardware such as a CPU and a memory equivalent to general computers.

Advantageous Effects of Invention

With the present invention, influence due to periodic body movement of a subject in an image of the subject formed using X-rays can be reduced and image quality can be improved. For example, according to various aspects of the present invention, image data of the subject can be formed while correcting the body movement periodic component related to the periodic body movement of the subject.

BEST MODE FOR CARRYING OUT THE INVENTION

Figure 1:
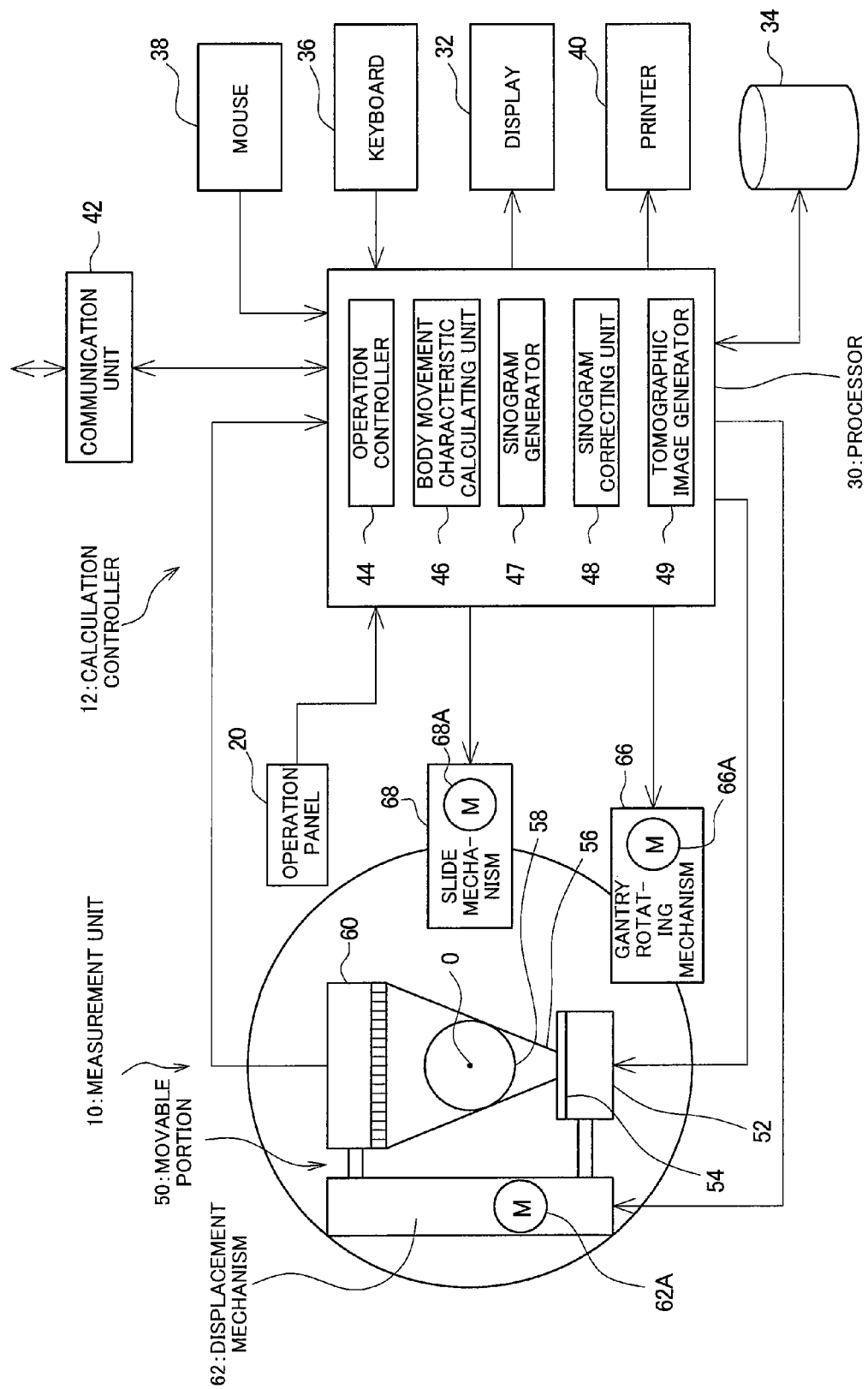
FIG. 1 is a functional block diagram of an X-ray CT device which is a representative example of an X-ray image formation device.
Figure 2:
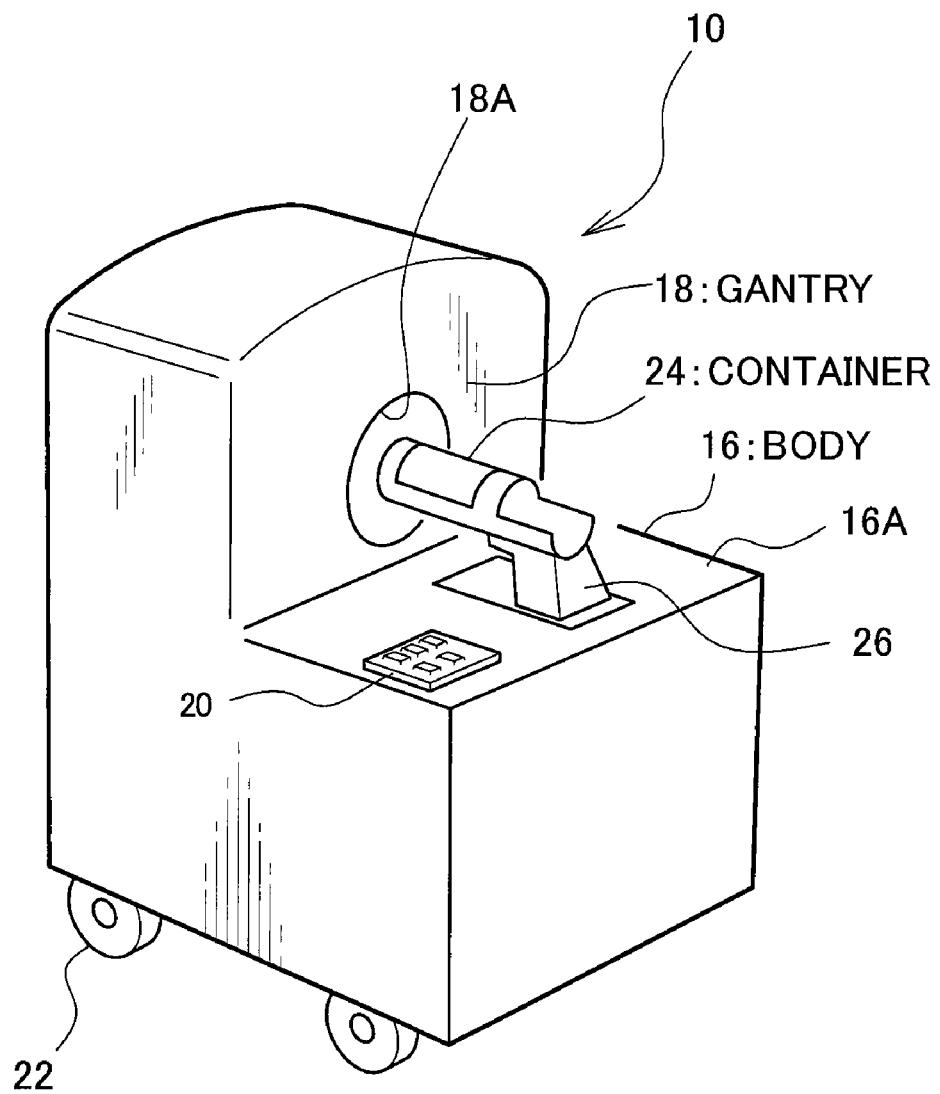
FIG. 2 is a perspective view of a measurement unit.

FIG. 1 is a diagram for explaining a preferred embodiment of the present invention, and is a functional block diagram of an X-ray CT device which is a representative example of an X-ray image formation device according to the present invention. FIG. 2 is a perspective view of a measurement unit 10 of the X-ray CT device shown in FIG. 1. The X-ray CT device of the preferred embodiment of the present invention shown in FIG. 1 will now be described while referring also to FIG. 2 as necessary.

The X-ray CT device is a device which generates a tomographic image (CT image) of a subject based on projection data obtained by radiating X-rays to the subject. The X-ray CT device of the present embodiment has a function to detect a characteristic of a body movement of the subject such as, for example, a period of body movement, in addition to a generation function of the tomographic image. With the detected body movement characteristic, generation of a more preferable tomographic image is enabled.

The X-ray CT device of the present embodiment has a structure preferable for a case where the subject is a small animal such as a mouse, rat, guinea pig, hamster, etc. used in, for example, animal tests. Alternatively, there may be employed a configuration in which structures of a gantry 18 and a container 24 are changed when the subject is a human or the like.

The X-ray CT device shown in FIG. 1 is mainly divided into a measurement unit 10 which obtains projection data, and a calculation controller 12 which controls driving of the measurement unit 10 and executes various calculations based on the obtained projection data.

With reference to FIG. 2, a body 16 having the gantry 18 is provided in the measurement unit 10. An opening is formed on an upper surface 16A of the body 16, and an arm 26 protrudes in the upward direction through the opening. The arm 26 forms a part of a slide mechanism 68, is connected to the container 24, and causes the container 24 to slide-move (moving scan) along a direction of a center axis of rotation.

Meanwhile, a measurement unit comprising an X-ray generator 52 and an X-ray detector 60 is stored in the gantry 18. The measurement unit rotationally moves around a center axis of rotation. A hollow portion 18A is formed in the center section of the gantry 18 along the direction of the center axis of rotation. The hollow portion 18A is of a non-through type, but may alternatively be of a through type.

The container 24 is a capsule storing a subject (small animal or tissues excised from the small animal), and in the present embodiment has an approximate hollow circular tube shape. The container 24 is placed with the center axis of the container matching the center axis of rotation. More specifically, a base end of the container 24 is mounted in a detachable manner on an upper end of the arm 26 described above. In this case, as the detachment/attachment mechanism, various engagement mechanisms or screwing mechanisms may be employed. As described above, the container 24 has a hollow circular tube shape, and in the present embodiment one or a plurality of small animals are placed in the container 24. With such a structure, it is possible to prevent, for example, direct contact with the hair of the small animal on the gantry 18. In addition, it is possible to prevent a problem in which excretion and detached hair of the small animal are discharged to the outside. Moreover, because the small animal can be constrained in the container 24 by a fixing device, it is possible to prevent problems such as image shaking in the case when the CT image is re-constructed. It is desirable to prepare a plurality of types of containers having different sizes and shapes and to selectively use the container.

After the container 24 is mounted on the arm 26, the arm 26 is driven in the forward direction along the direction of the center axis of rotation, and, with this process, the container 24 is inserted into the hollow portion 18A of the gantry 18. In this process, the container 24 is positioned such that the X-ray beam is set at a measurement position in the subject. The measurement position is changed continuously or stepwise. As a result, numerous CT cross sections spatially aligned with a predetermined pitch are formed.

An operation panel 20 is provided over the upper surface 16A of the body 16, and comprises a plurality of switches, a display, etc. A user can manipulate an operation of the device in the measurement location using the operation panel 20. A plurality of casters 22 are provided below the body 16.

As shown in FIG. 1, in the measurement unit 10, the X-ray generator 52 is provided on one side and the X-ray detector 60 is provided on the other side with the center axis of rotation O therebetween. A collimator 54 is provided at the radiation side of the X-ray generator 52. The X-ray generator 52 radiates an X-ray beam 56 of an intensity corresponding to a supplied drive voltage. The X-ray beam has a widening shape or a fan shape (that is, a fan beam shape) as shown in FIG. 1. Meanwhile, the X-ray detector 60 is formed as an arrangement of a plurality (for example, 100) X-ray detecting elements in one line, and a light-receiving opening of X-rays is set according to an open angle of the X-ray beam 56. The arrangement of the plurality of X-ray detecting elements may be linear or may be an arc shape. In the present embodiment, an X-ray detecting element of high sensitivity type is used. The detected value at the X-ray detector 60 is output to a processor 30 as projection data. In FIG. 1, illustration of a voltage source connected to the X-ray generator 52, a signal processing circuit connected to the X-ray detector 60, etc. is omitted.

In FIG. 1, reference numeral 58 represents an effective field of view. The effective field of view is a circular region in which the CT image can be formed when the X-ray beam 56 is rotationally scanned. The effective field of view 58 is determined according to a positional relationship among the center axis of rotation, the X-ray generator 52, and the X-ray detector 60. In the present embodiment, because a displacement mechanism 62 is provided, the positional relationship can be changed, to mechanically change the magnification of the CT image.

Specifically, the X-ray generator 52 and the X-ray detector are connected to the displacement mechanism 62, and the displacement mechanism 62 displaces the X-ray generator 52 and the X-ray detector 60 (that is, the measurement unit) along the beam axis direction of the X-ray beam while maintaining the distance between the X-ray generator 52 and the X-ray detector 60. In this case, the center axis of rotation O does not change, and, thus, the measurement unit side can be moved while not moving the container at all, to achieve a change in the magnification. The displacement mechanism 62 comprises a motor 62A for generating a displacement force.

A gantry rotating mechanism 66 is a mechanism which rotationally drives the entirety of the structures including the displacement mechanism mounted on a rotational base, by rotating the rotational base. Because the measurement unit is mounted on the displacement mechanism 62, the measurement unit positioned at a desired position by the displacement mechanism 62 is rotationally driven while maintaining the position. The gantry rotating mechanism 66 comprises a motor 66A for generating its drive force.

The slide mechanism 68 is a movement mechanism which slide-moves the arm 26 shown in FIG. 2, and the drive force of the slide mechanism 68 is generated by a motor 68A. As described above, the operation panel 20 is provided on the upper surface of the body. Alternatively, there may be employed a configuration in which the operation panel 20 is connected to a local controller (not shown) provided on the side of the measurement unit 10, and the local controller and the calculation controller 12 communicate with each other.

FIG. 1 shows various mechanisms 62, 66, 68, etc., and it is desirable to provide sensors for detecting a position or a change in position by these mechanisms. It is desirable for the calculation controller 12 to execute a feedback control based on output signals of the sensors. In addition, the change of magnification by the displacement mechanism 62 may be achieved by user input, or, for example, a size of the subject or a size of the container may be automatically detected and the magnification may be automatically set based on the detected data. In addition, in a case where the type or the like of the container is registered in advance, the magnification may be set using the registered information. In addition, in the example configuration of FIG. 1, the slide mechanism comprises the motor 68A as a drive source, but alternatively, the slide force may be artificially generated.

Next, the calculation controller 12 will be described. A display 32, a storage device 34, a keyboard 36, a mouse 38, a printer 40, or the like are connected to the processor 30. In addition, a communication unit 42 for communicating with an external device through a network is connected.

The processor 30 comprises hardware such as a CPU and a memory, and software such as a controlling program. FIG. 1 shows representative functions realized by a co-operation of the hardware and the software. That is, the processor 30 comprises an operation controller 44, a body movement characteristic calculating unit 46, a sinogram generator 47, a sinogram correcting unit 48, a tomographic image generator 49, etc. Alternatively, a computer may be operated as the processor 30 using programs corresponding to these functions.

The operation controller 44 controls driving of the measurement unit 10. More specifically, the operation controller 44 drives and controls the gantry rotating mechanism 66, X-ray generator 52, X-ray detector 60, etc., to execute CT imaging. CT imaging is an imaging operation for generating a tomographic image, and is an operation in which X-rays are radiated and detected while the X-ray generator 52 and the X-ray detector 60 are rotated with respect to the subject. In the related art, in most cases, the CT imaging is executed once for each imaging site. In the present embodiment, however, as will be described later in more detail, a plurality of CT imaging operations are executed for each imaging site. Projection data obtained as a result of the CT imaging are output to the body movement characteristic calculating unit 46 and the sinogram generator 47.

The body movement characteristic calculating unit 46 calculates a characteristic of body movement of the subject based on the projection data obtained by CT imaging. Here, the body movement refers to a periodic movement of the subject, and, for example, a respiratory movement, a heartbeat movement, etc. correspond to the body movement. As for the characteristic of the body movement, for example, a period of the body movement, continued time of displacement of the imaging target due to respiratory movement (variation time), etc. correspond to the characteristic. The calculation of the body movement characteristic by the body movement characteristic calculating unit 46 is basically executed for each CT imaging operation. The body movement characteristic calculated for each CT imaging is used for controlling the start timing of the CT imaging operation to be next executed, for example. When there is no next CT imaging operation or the imaging site is to be changed at the next CT imaging operation, the calculation of the body movement characteristic is unnecessary. In other words, when N CT imaging operations are to be executed for one imaging site, the body movement characteristic does not need to be calculated at the Nth CT imaging operation.

The sinogram generator 47 is an element which generates the sinogram, as the name suggests. The sinogram is arrangement of the projection data obtained by the CT imaging in the order of rotational angle, and will now be described with reference to FIG. 3.

Figure 3:
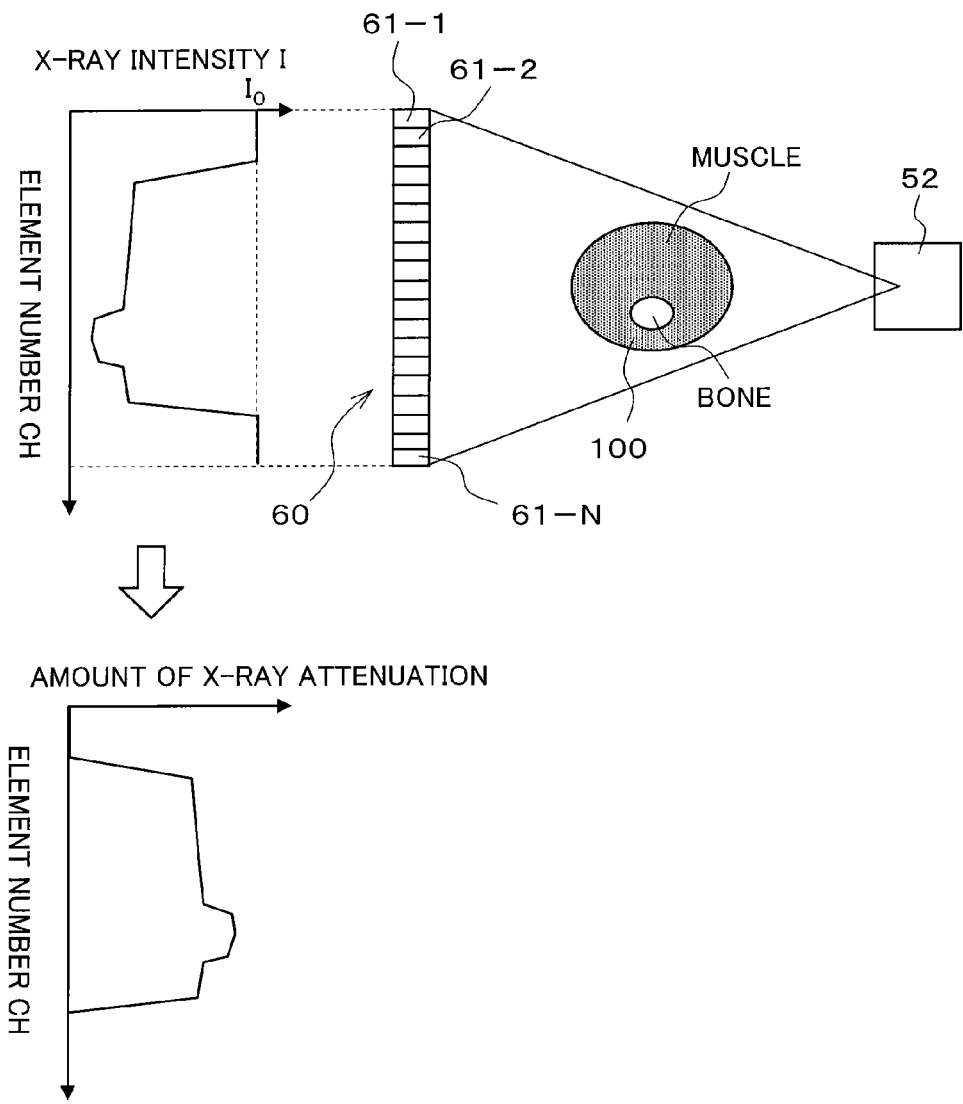
FIG. 3 is a diagram for explaining a basic principle of CT imaging.

FIG. 3 is a diagram for explaining a basic principle of CT imaging. As already described, in the measurement unit 10 (FIG. 1), the X-ray generator 52 and the X-ray detector 60 are placed opposing each other with the subject 100 therebetween. After a part of the X-rays radiated from the X-ray generator 52 is absorbed by the subject 100, the X-rays reach the X-ray detector 60. Detecting elements 61-1, 61-2, . . . 61-N provided in the X-ray detector 60 detect intensity I of the X-rays. Data obtained by converting the detected X-ray intensity I into an amount of X-ray attenuation R are the projection data. The amount of X-ray attenuation R is calculated with $R=\log_e(I_0/I)$ based on the intensity I of the radiated X-rays and the detected intensity I of the X-rays.

In the present embodiment, in the CT imaging of one operation, the X-ray generator 52 and the X-ray detector 60 are rotated 180 degrees with respect to the subject 100. During the rotation, the projection data are output for each predefined rotational angle. The sinogram is formed for each CT imaging operation.

Figure 4:
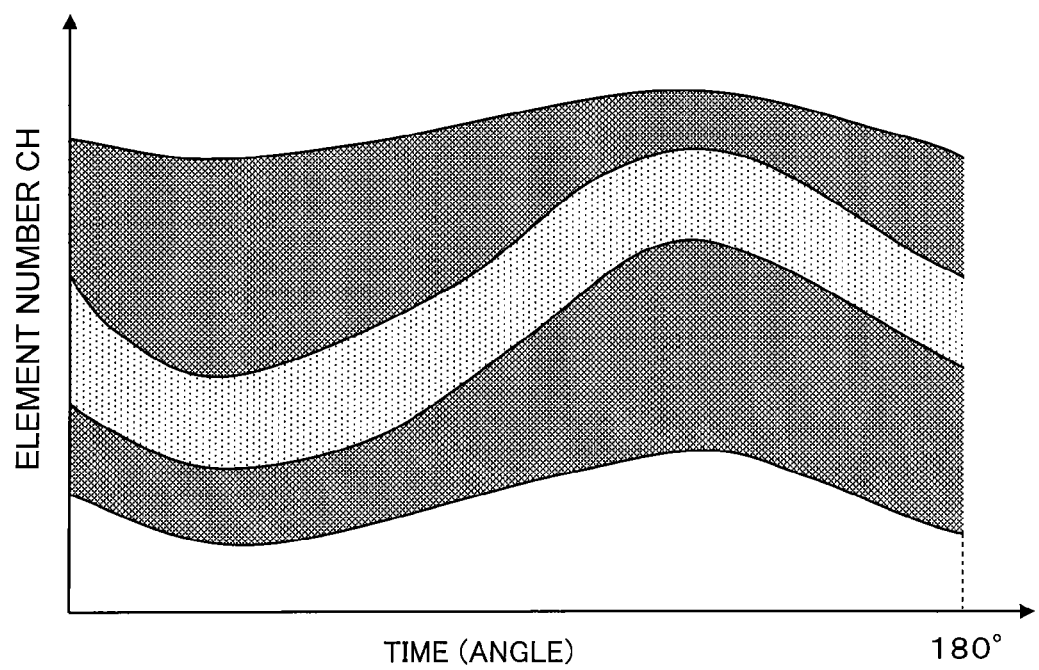
FIG. 4 is an image diagram of a sinogram.

FIG. 4 is an image diagram of the sinogram in which an image is formed with the amount of X-ray attenuation R being set as a brightness value. In the sinogram, projection data obtained for each predefined rotational angle are arranged with the rotational angle along the horizontal axis and element number along the vertical axis.

Referring again to FIG. 1, as already described, in the present embodiment, the CT imaging is executed a plurality of times for each imaging site, and the sinogram generator 47 generates the sinogram for each CT imaging operation. Therefore, a plurality of sinograms are generated for each imaging site. The plurality of sinograms are output to the sinogram correcting unit 48.

The sinogram correcting unit 48 corrects the calculated sinogram to remove or reduce the influence of the body movement. The thus-corrected sinogram is output as a corrected sinogram to the tomographic image generator 49.

The tomographic image generator 49 generates a tomographic image based on the corrected sinogram. For the generation of the tomographic image based on sinogram, well-known techniques of related art may be employed, and, thus, the process will not be described here in detail. The obtained tomographic image is displayed on the display 32. The user diagnoses or the like the state of the inside of the subject based on the tomographic image displayed on the display 32.

Next, an operation of the X-ray CT device will be described in detail. As already described, the X-ray CT device of the present embodiment calculates the body movement characteristic based on the projection data obtained as a result of the CT imaging. A reason for this will be briefly described exemplifying the respiratory movement.

Figure 5:
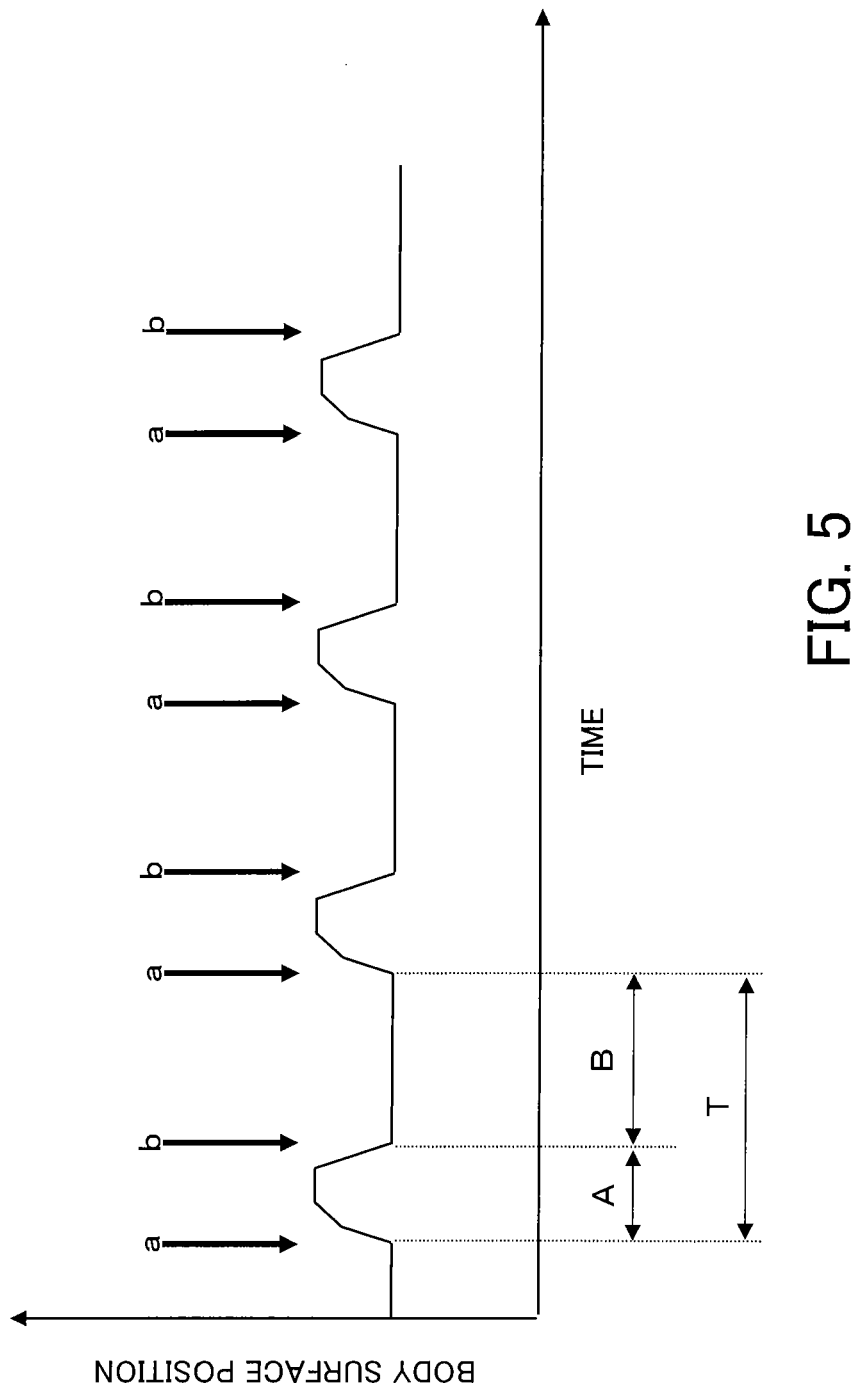
FIG. 5 is a diagram showing a movement of a body surface of a chest portion of the subject caused by respiration.

FIG. 5 is a graph schematically showing a variation of position of a body surface around a chest portion of a rat put to sleep by anesthesia. In FIG. 5, an arrow a represents a start timing of a respiratory operation to take breath in, and an arrow b represents a start timing of a respiratory operation to expel breath out. As is clear from FIG. 5, although the chest portion of the animal is almost stationary after the completion of the respiration to expel breath out, the chest portion moves during the respiration to take breath in. In the following, a period B from a timing b to timing a in which the chest portion is approximately stationary is described as a stationary period B and a period A from the timing a to the timing b in which the chest portion is varying is described as a variation period A. Naturally, the variation of the subject at the variation period A affects the projection data to be detected. More specifically, the amount of X-ray attenuation detected during the variation period A tends to be lower compared to the amount of X-ray attenuation detected during the stationary period.

Therefore, in the sinogram generated based on the projection data obtained by the CT imaging executed during the respiratory movement, a portion in which the amount of X-ray attenuation is reduced (brightness is reduced) would periodically appear. The portion of the reduced amount of X-ray attenuation corresponds to the variation period A. If the tomographic image is generated based on the projection data in which the influence of the movement of the subject in the variation period A remains, a virtual image which is called a motion artifact appears in the tomographic image.

In consideration of this, in the related art, techniques are known in which the respiration of the subject is detected, and, using the detection result, the CT imaging is executed in synchronization with the body movement. However, in such a technique of the related art, a dedicated respiratory sensor has been used for detecting the respiratory movement. Use of the respiratory sensor not only has a problem that cost increases, but also has a problem that an extra work is necessary for detachment/attachment of the respiratory sensor on the subject. In addition, there also had been a problem in which the respiratory sensor mounted on the subject is drawn in the tomographic image, and, consequently, the reliability of the diagnosis is reduced.

On the other hand, in the present embodiment, the characteristic of respiration is calculated based on a detection result obtained by the CT imaging without use of the dedicated respiration sensor. A process for calculating the body movement characteristic will now be described in detail.

As already described, in the CT imaging, projection data as shown in FIG. 3 are collected for each predefined rotational angle. The body movement characteristic calculating unit 46 extracts a data variation caused by respiratory movement from the projection data collected for each predefined rotational angle, and based on the extracted result, calculates the period or the like of the respiratory movement. The data variation caused by the respiratory movement is extracted, for example, through the following steps.

As shown in FIG. 3, the plurality of X-ray detecting elements 61-1, 61-2, . . . 61-N are provided in the X-ray detector 60, and an X-ray intensity is detected for each of the X-ray detecting elements 61-1, 61-2, . . . 61-N. The projection data are data in which the X-ray intensity is converted into an amount of X-ray attenuation. Therefore, projection data of one operation include N amounts of X-ray attenuation corresponding to the number of X-ray detecting elements.

When the data variation caused by the respiratory movement is extracted, the body movement characteristic calculating unit 46 (FIG. 1) calculates an average Rave of the N amounts of X-ray attenuation for each predefined rotational angle.

Figure 6:
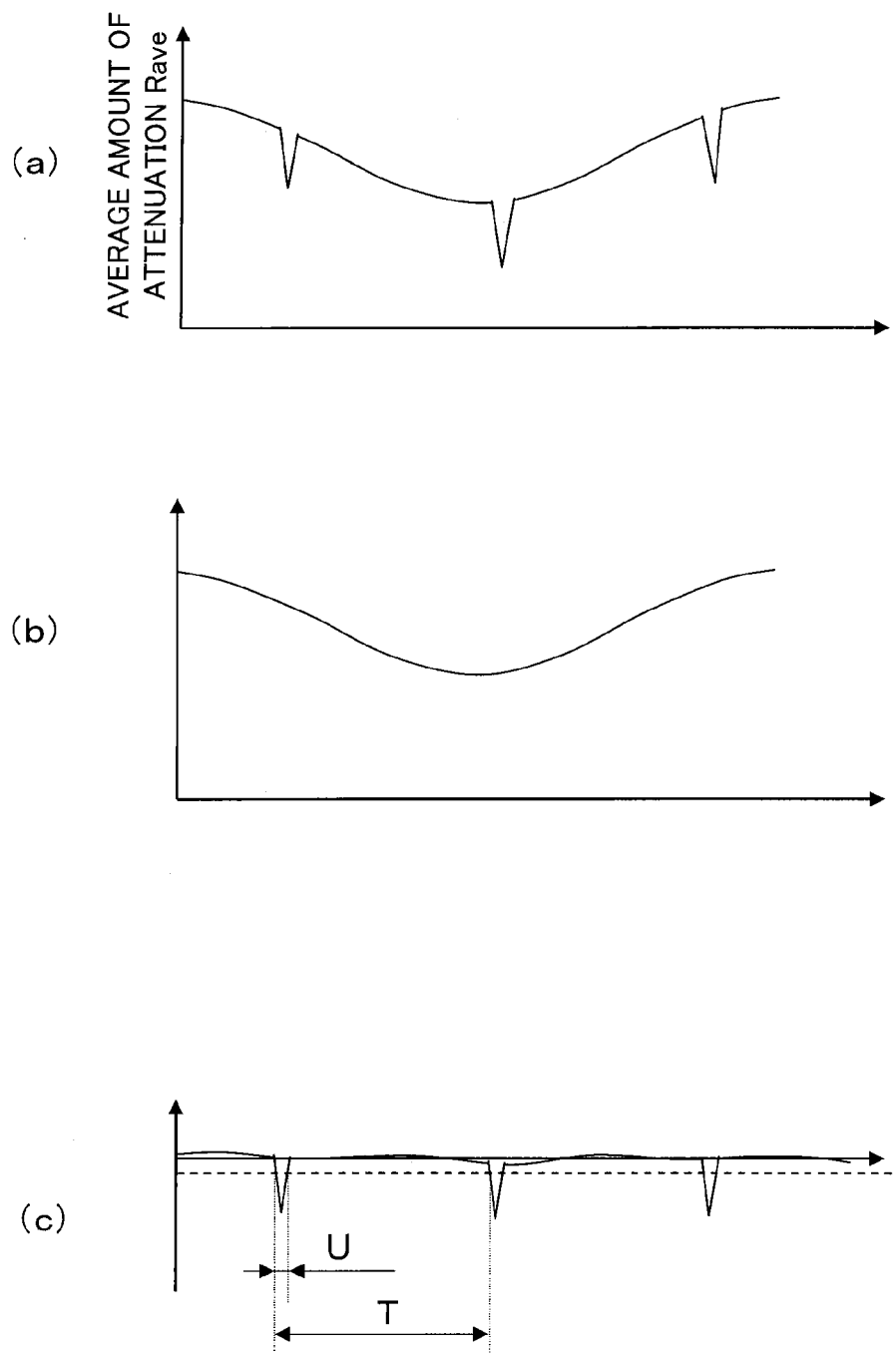
FIG. 6 is a graph showing an average of an amount of X-ray attenuation.

FIG. 6 is a diagram for explaining the calculation of the average Rave of the amounts of X-ray attenuation. FIG. 6(a) is a graph showing a calculated average Rave of the amounts of X-ray attenuation. In FIG. 6(a), the horizontal axis represents a detection time and the vertical axis represents the average Rave of the amounts of X-ray attenuation.

As shown in FIG. 6(a), normally, an average Rave of the amount of X-ray attenuation varies in an approximate sine wave shape, with periodic occurrence of a peak in the downward direction. The variation in the sine wave shape is caused by rotation of the measurement unit (the X-ray generator 52 and the X-ray detector 60 in FIG. 1). In addition, the downward peak which periodically occurs is caused by the respiratory movement. Therefore, by extracting the downward peak, it is possible to extract the data variation caused by the respiratory movement. However, in a state where the data variation caused by the rotation of the measurement unit is still mixed, difficulty is encountered in extracting only the data variation caused by the respiratory movement.

In consideration of this, the body movement characteristic calculating unit 46 (FIG. 1) removes or reduces the data variation caused by the rotation of the measurement unit from an approximated value of the average Rave of the amount of X-ray attenuation. More specifically, the body movement characteristic calculating unit 46 calculates an approximated curve of the average Rave of the amount of attenuation, and calculates a difference between the approximated curve and the average Rave of the amount of attenuation. For the calculation of the approximated curve, for example, techniques well known in the related art may be used, such as median approximation, moving average, etc.

FIG. 6(b) is a diagram showing an example of the calculated approximated curve. FIG. 6(c) is a diagram showing the calculated difference. As is clear from FIG. 6(c), by calculating the difference between the average Rave of the amount of attenuation and the approximated curve, it is possible to obtain data in which the data variation caused by the measurement unit; that is, the variation in the approximate sine wave shape, is significantly reduced.

When the body movement characteristic calculating unit 46 (FIG. 1) obtains the difference data, the body movement characteristic calculating unit 46 calculates the occurrence period of the downward peak caused in the average Rave of the amount of X-ray attenuation and a peak width by binarizing the difference data with a predetermined threshold value or the like. The obtained occurrence period of the peak is temporarily stored in the storage device 34 (FIG. 1) as a respiration period T and the obtained peak width is temporarily stored in the storage device 34 as a variation period U.

As is clear from the above description, according to the present embodiment, the period or the like of the respiratory movement can be obtained from projection data obtained in the CT imaging. In other words, it is not necessary to provide a dedicated sensor for detecting the period of the respiratory movement or the like. As a result, the cost required for the respiration sensor can be reduced, as can the work related to the handling of the respiration sensor. In addition, the reduction in the reliability of diagnosis due to drawing of the respiration sensor in the tomographic image can be prevented. In addition, the calculation of the body movement characteristic is executed based on data obtained in the CT imaging which is required for formation of the tomographic image. In other words, according to the present embodiment, it is not necessary to separately execute redundant X-ray radiation for calculating the body movement characteristic. As a result, it is possible to prevent adverse influences due to exposure and to prevent increase in the processing time.

In the above description, the body movement characteristic is calculated based on the average Rave of the amount of X-ray attenuation. Alternatively, the body movement characteristic may be calculated based on other parameters, such as an accumulated value of the amount of X-ray attenuation, accumulated value or average of the X-ray intensity, etc., so long as the parameter is a parameter which indicates a tendency of variation of the X-ray detection result. In addition, the body movement characteristic may be calculated based on a position of a center of gravity M of the amount R of X-ray attenuation calculated by the following Equation (1). In Equation (1), $R_{CH}$ is the amount of X-ray attenuation detected at an element number CH. In addition, in the above description, the case of the respiratory movement is exemplified, but the present embodiment can alternatively be applied to characteristic detection of other body movement, such as the heartbeat movement of the heart, so long as the body movement occurs periodically.

[Equation 1]

$$M = \frac{\sum_{CH}(R_{CH} \times CH)}{\sum_{CH} R_{CH}} \qquad \text{(equation 1)}$$

Next, a respiration synchronization imaging operation executed in the present embodiment will be described. For portions (structures) already shown in FIG. 1, the reference numerals of FIG. 1 will be used in the following description. As already described, when the position of the subject varies due to respiration during the CT imaging, artifacts arise in the tomographic image. In order to avoid such a problem, it is proposed to synchronize the CT imaging and the respiratory movement in order to execute the CT imaging during the period in which the subject is almost stationary. This technique is effective when the time required for one CT imaging operation; that is, time required for rotation of 180 degrees of the measurement unit, is sufficiently shorter than the stationary time of the subject. However, in order to enable CT imaging at such a high speed, a high-performance, high-cost driving mechanism or the like must be provided, which results in an increase in the cost of the X-ray CT device. On the other hand, there is a problem in that, when the time required for one CT imaging operation is longer than the stationary time of the subject, the technique cannot be employed.

In the present embodiment, in order to solve these problems, the CT imaging operation is executed a plurality of times for one imaging site while shifting the phase of the body movement. Based on the data obtained from the plurality of CT imaging operations, there is generated a tomographic image in which the influence of the body movement is removed or reduced. More specifically, the tomographic image is obtained by the following process. In the following, for purpose of explanation, an example case is described in which the variation period is less than T/2 when the respiratory period is T.

In order to generate the tomographic image, the operation controller 44 drives the rotating mechanism 66, measurement unit, etc., to execute the CT image of the first operation.

Specifically, the operation controller 44 causes execution of the radiation and detection of X-ray while the measurement unit is rotated with respect to the subject. When the CT imaging of the first operation is executed, as already described, the body movement characteristic calculating unit 46 calculates the period T of the respiration and the variation period U based on the projection data obtained in this CT imaging. In addition, the sinogram generator 47 arranges the projection data obtained in this case in the order of the rotational angle, to generate a first sinogram.

Figure 7:
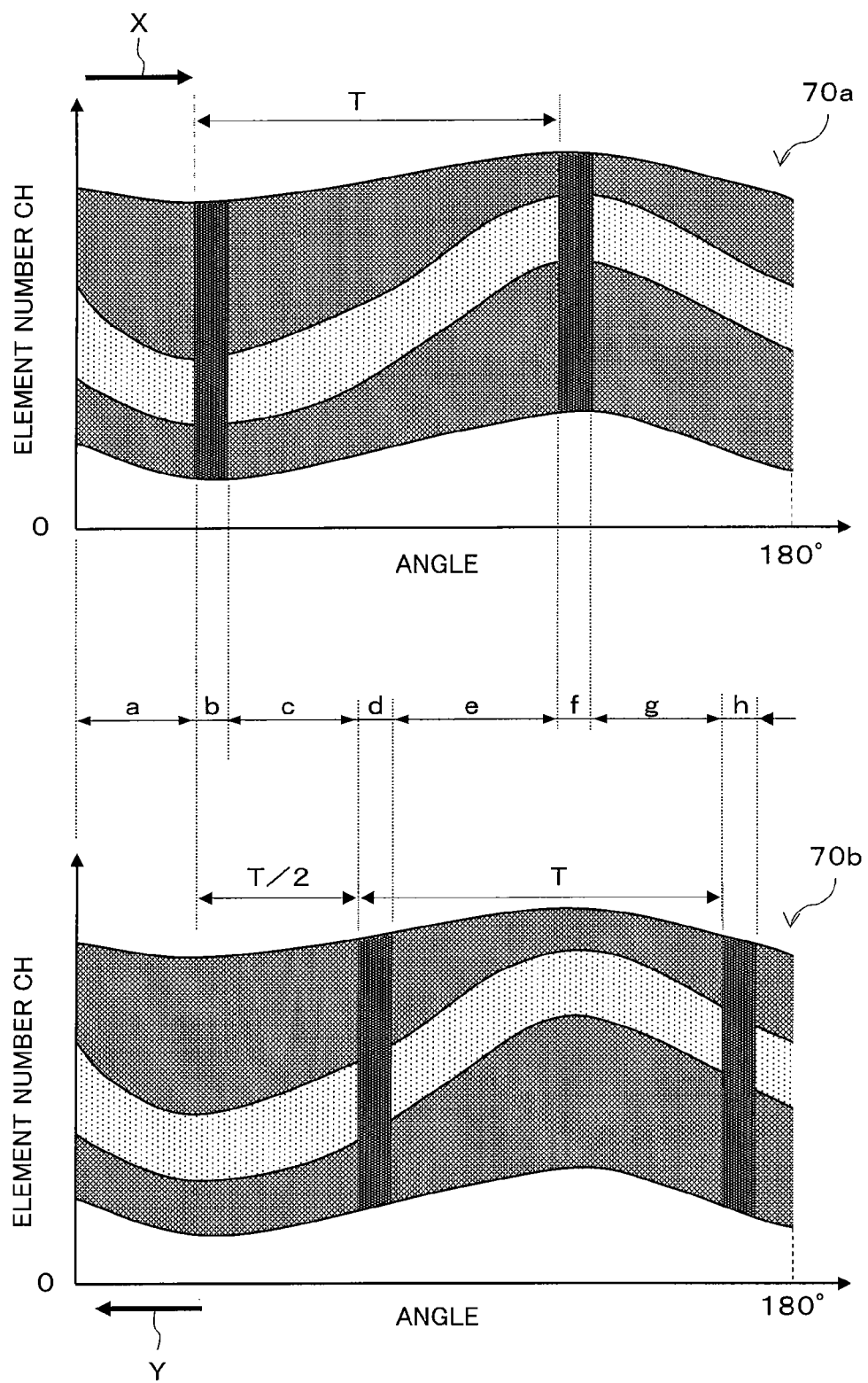
FIG. 7 is a diagram for explaining a sinogram formed in a preferred embodiment of the present invention.

FIG. 7 is a diagram for explaining the sinogram formed in the present embodiment. An upper part of FIG. 7 shows an image of a first sinogram 70a obtained in the first CT imaging operation.

When the first CT imaging operation is completed, next, the operation controller 44 drives the rotating mechanism 66, the measurement unit, etc., to cause execution of a second CT imaging operation. A start timing of the second CT imaging operation is controlled based on the body movement characteristic calculated from the result of the first CT imaging operation. More specifically, the timing of the second CT imaging operation is controlled such that the phase of the respiration with respect to the rotation of the measurement unit is inverted as compared with the first CT imaging operation. In other words, the timing is controlled for execution of the first CT imaging operation such that a second sinogram 70b generated from the projection data obtained in the second CT imaging operation has the timing of the respiration shifted by a half period (T/2) as compared with the first sinogram 70a, as shown in a lower part of FIG. 7.

In the present embodiment, every time the CT imaging operation is executed, a direction of rotation of the measurement unit is reversed. Specifically, after the measurement unit is rotated in the clockwise direction from 0 degree to 180 degrees in the first CT imaging operation, the measurement unit is rotated in the counterclockwise direction from 180 degrees to 0 degree in the second CT imaging operation. In this case, the flow of time in the first sinogram 70a is shown by an arrow X in FIG. 7, and the direction of increase of the rotational angle and the direction of elapse of time for the detection time are identical. On the other hand, in the second CT imaging operation, the rotational angle is reduced as the detection time elapses. Therefore, the direction of elapse of time for the detection time in the second sinogram 70b arranged in the order of the rotational angle is in the opposite direction from the direction of increase in the rotational angle, as shown by an arrow Y. When the second CT imaging operation is executed, the timing must be controlled in consideration of this relationship between the elapsed time and the rotational angle.

Figure 8:
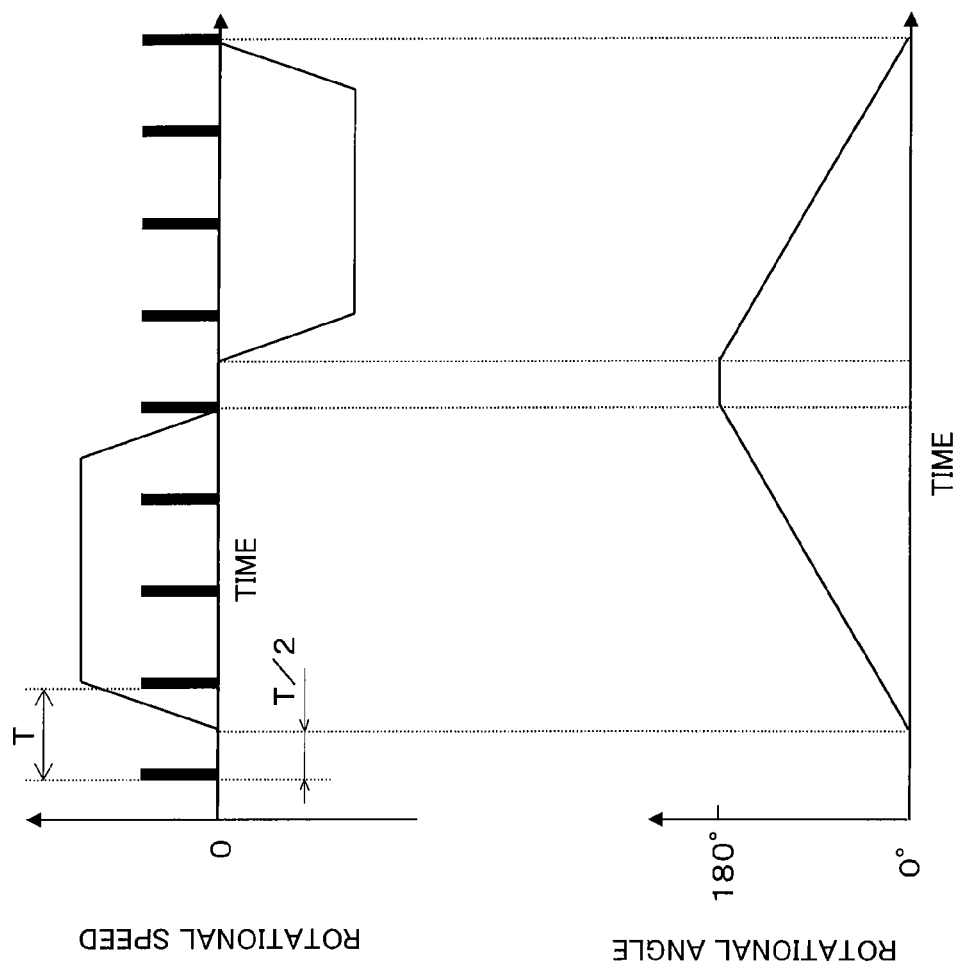
FIG. 8 is a diagram for explaining a timing control of CT imaging in a preferred embodiment of the present invention.
Figure 9:
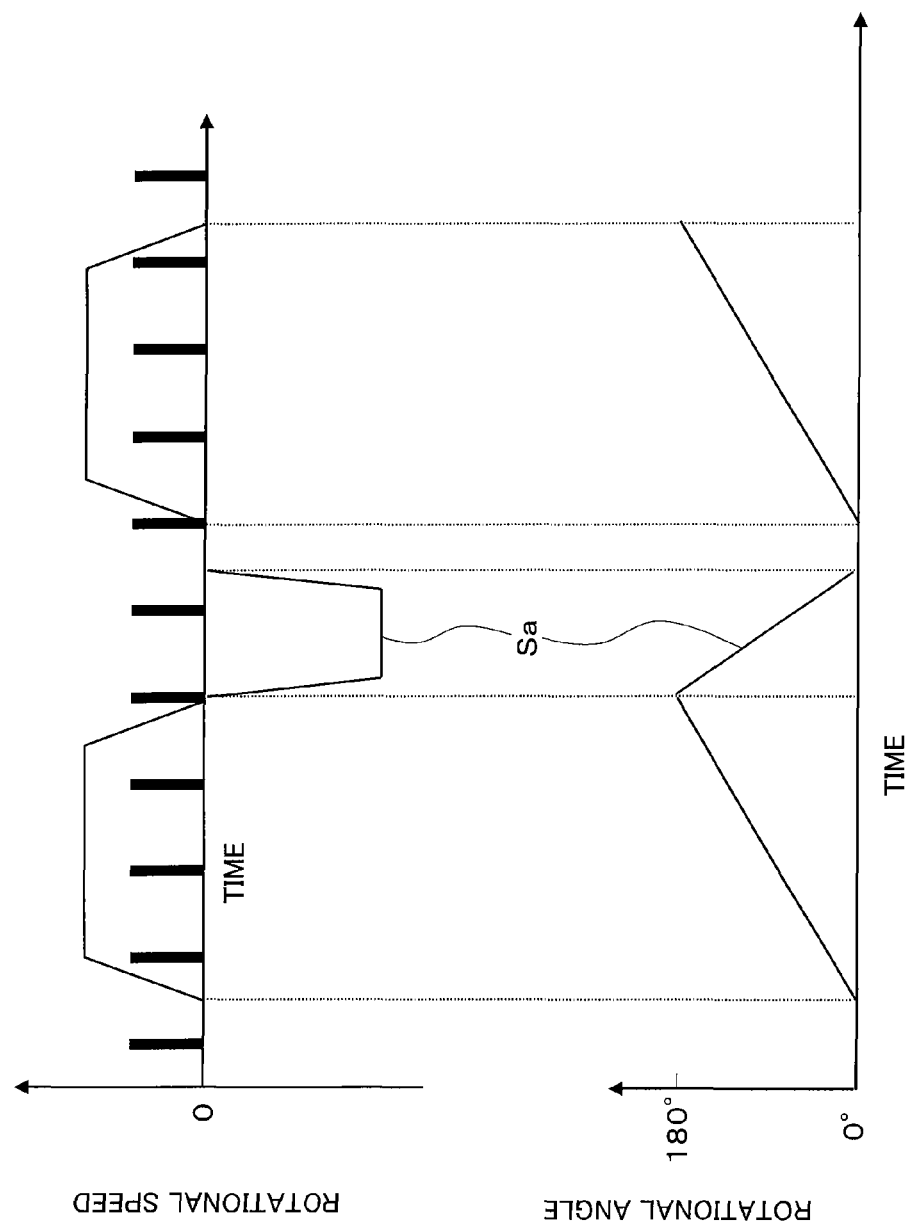
FIG. 9 is a diagram for explaining a timing control of CT imaging in a preferred embodiment of the present invention.

FIGS. 8 and 9 are diagrams for explaining the timing control of the CT imaging in the present embodiment. A graph on an upper side of FIG. 8 shows a rotational speed of the measurement unit, and a graph on a lower side of FIG. 8 shows a rotational angle of the measurement unit. In FIG. 8, a wide vertical line represents a respiration timing. As shown in FIG. 8, the first CT measurement operation is started after T/2 has elapsed from the respiration start timing. In this case, the driving for the second CT imaging operation must be controlled such that the completion time of the CT imaging; that is, the time when the rotational angle reaches 0, is the respiration start timing.

In the present embodiment, the rotation direction of the measurement unit is reversed every CT imaging operation, but alternatively, as shown in FIG. 9, a step Sato return to the initial position after each CT imaging operation may be added, so that the rotation direction during CT imaging is always in the same direction.

The sinogram correcting unit 48 generates a corrected sinogram in which the data variation caused by the respiratory movement is removed or reduced, based on the sinograms 70a and 70b obtained by two CT imaging operations. As a method of generating the corrected sinogram, for example, there may be considered a method in which the data of the variation period in one of the two sinograms 70a and 70b are supplemented by the other sinogram. More specifically, with reference to FIG. 7, data of periods b and f corresponding to the variation period in the first sinogram 70a may be replaced with the data of the periods b and f of the second sinogram, to calculate the corrected sinogram. In this case, for a period in which the subject is stationary for both the first time and the second time, it is desirable to average the two sinograms 70a and 70b. In other words, in FIG. 7, for periods a, c, e, and g, average values of the first sinogram 70a and the second sinogram 70b are desirably used. With the use of the average value in this manner, it is possible to reduce the influences of noise and to obtain a more preferable tomographic image.

The variation period (periods b, d, and f) in each of the sinograms 70a and 70 may be calculated based on the body movement characteristic calculated by the body movement characteristic calculating unit 46, but is desirably calculated based on the projection data obtained from the first and second CT imaging operations.

Figure 10:
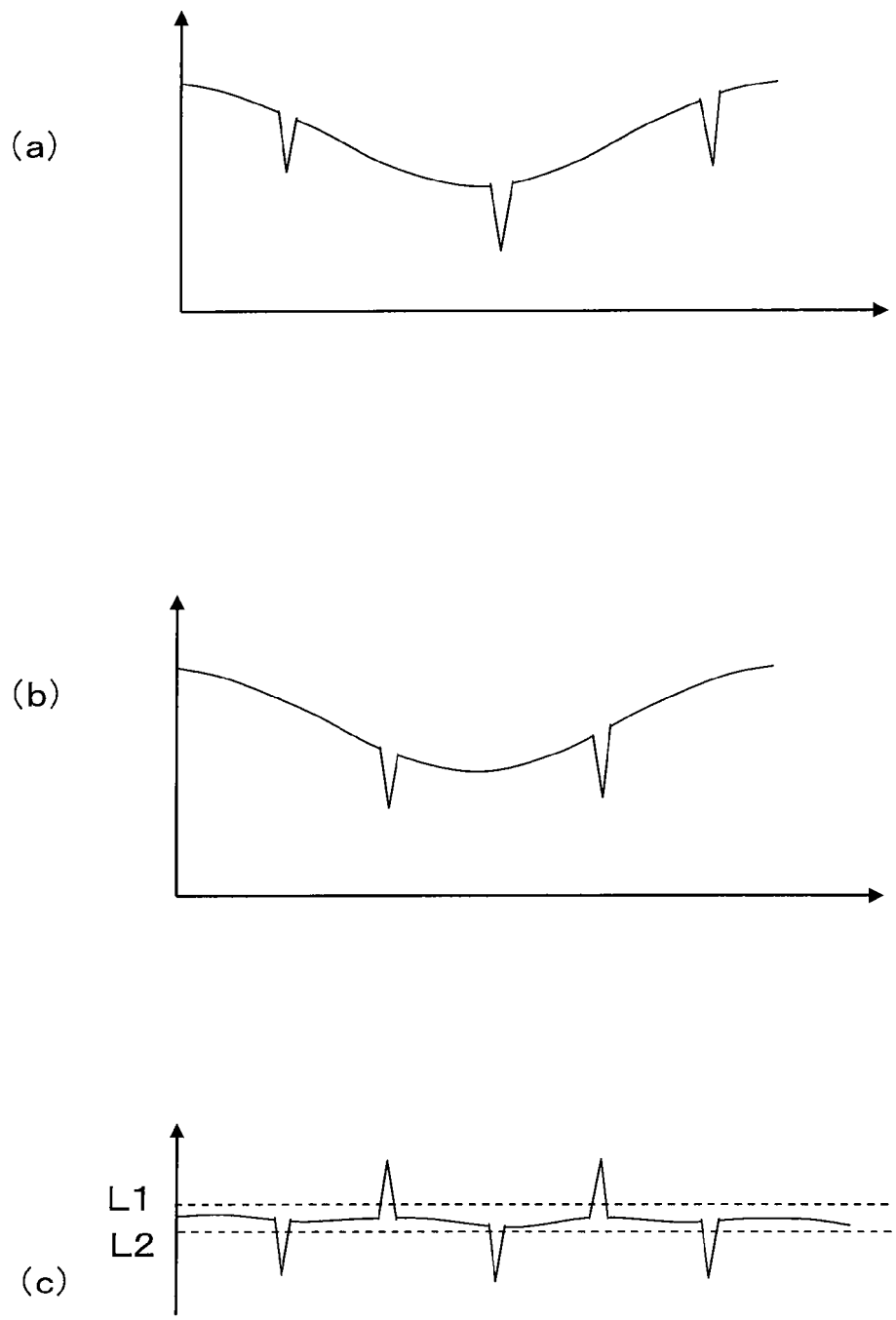
FIG. 10 is a diagram for explaining a variation period obtained from projection data of CT imaging.

FIG. 10 is a diagram for explaining the variation period obtained based on the projection data of the first and second CT imaging operations. An average $Rave_1$ of the amount of X-ray attenuation at the first CT imaging operation (FIG. 10(a)) and an average $Rave_2$ of the amount of X-ray attenuation at the second CT imaging operation (FIG. 10(b)) are calculated. Then, a difference between the two averages of the amount of X-ray attenuation is calculated. The conditions in the first and second CT imaging operations other than the phase of the respiration, such as, for example, the imaging site and the intensity of X-ray to be radiated, are assumed to be identical. Therefore, the difference in the averages of the amount of X-ray attenuation is data in which only the data variation portion caused by the respiration remains, as shown in FIG. 10(c). The processor 30 compares the obtained difference data and predefined threshold values L1 and L2, or the like, to identify the variation period (periods b, d, and f). By identifying the variation period based on the projection data obtained at the first and second CT imaging operations in this manner, it is possible to accurately identify the variation period even when the respiration period and variation time vary between the first CT imaging operation and the second CT imaging operation.

In addition, as another method of generating the corrected sinogram, data in which the first sinogram 70a and the second sinogram 70b are averaged may be calculated as the corrected sinogram. In this method, although the data variation caused by the respiration movement cannot be completely removed, the data variation may be reduced to half. As a result, the influence of the respiration movement can be reduced, and a more preferable tomographic image as compared with the related art can be obtained.

When the corrected sinogram is generated, the tomographic image generator 49 generates a tomographic image based on the corrected sinogram. In this process, the data variation caused by respiration is removed or reduced in the corrected sinogram. Therefore, based on the corrected sinogram, a preferable tomographic image having a reduced amount of motion artifacts can be obtained.

In addition, in the present embodiment, in the corrected sinogram formed based on the sinograms obtained by two CT imaging operations which is set as a nominal number of operations, when the data variation component due to respiration remains in an overlapping manner on the same angle, one more round of CT imaging operations is added. The corrected sinogram is further corrected using the sinogram obtained by the additional CT imaging operations.

Figure 11:
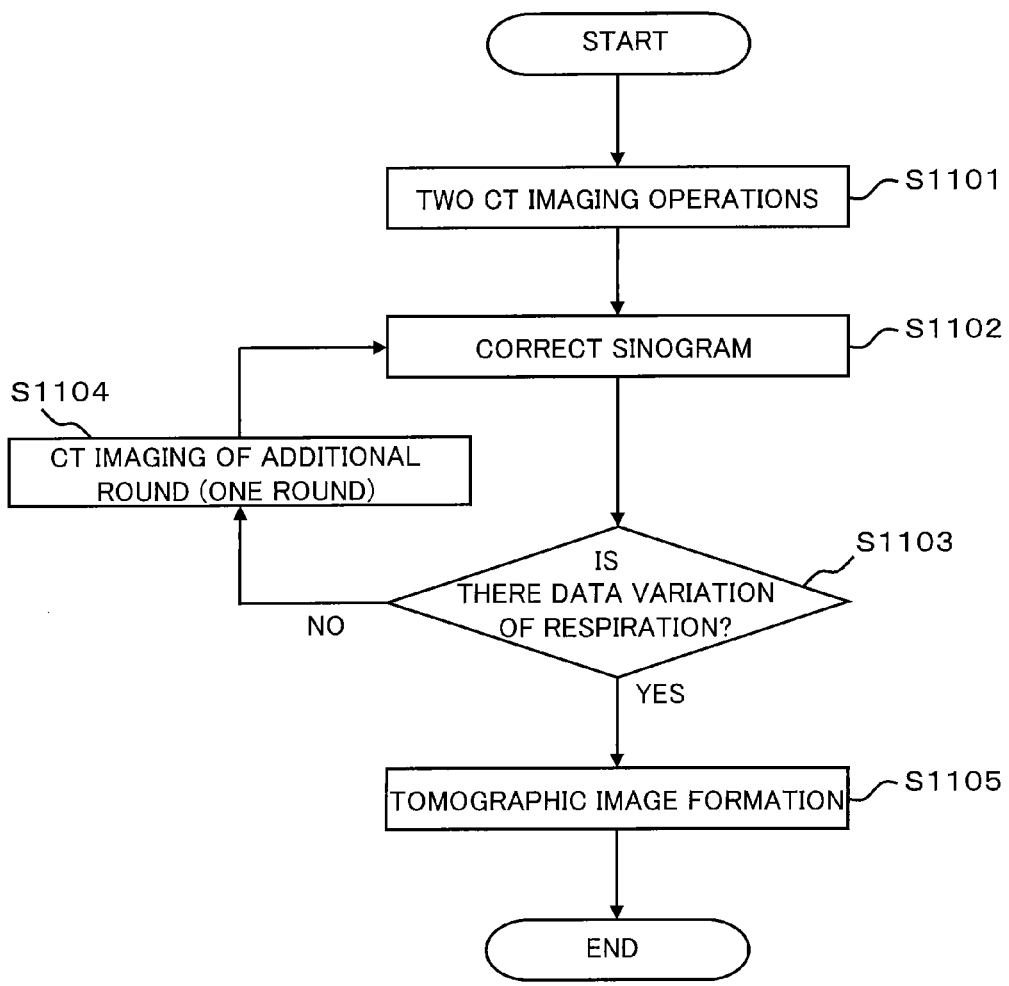
FIG. 11 is a flowchart showing an image formation process in a preferred embodiment of the present invention.

FIG. 11 is a flowchart for explaining a formation process of the tomographic image in the present embodiment. First, as already explained, two CT imaging operations are executed, which is set as the normal number of operations (S1101), and the sinogram is corrected based on the sinograms obtained by the two CT imaging operations (S1102). Because the first and second CT imaging operations are controlled such that the periods of the data variation caused by the respiration are shifted from each other, normally, the data variation caused by the respiration is removed with two CT imaging operations. Because of this, in step S1103, it is judged that there is no data variation caused by the respiration, and the tomographic image is formed based on the corrected sinogram obtained by the two CT imaging operations (S1105).

However, the period of respiration of the subject is not always the same, and, for example, the period of respiration of the subject may be shifted between two CT imaging operations, which is set as the normal number of rounds. Depending on the degree of shift of the period of respiration of the subject, there may be cases where, even though the two CT imaging operations are controlled such that the periods of data variation caused by respiration are shifted from each other, the data variation component caused by respiration is overlapped on the same angle.

For example, in FIG. 7, if the variation period of period d in the second sinogram 70b (variation period caused by respiration) is shifted to the position of the period b due to variation of the respiration period of the subject, the variation period of the first sinogram 70a and the variation period of the second sinogram 70b are overlapped with each other at the angle of the period b, and thus, the variation period cannot be completely removed.

Therefore, in the present embodiment, as shown in the flowchart of FIG. 11, when the data variation component remains in an overlapping manner on the same angle, in step S1103, it is judged that there is data variation caused by respiration, and an additional round of CT imaging is executed (S1104). In this additional round of CT imaging, the start timing or the like of the additional CT imaging operation is controlled such that the variation period is shifted from the angle where the variation periods are overlapped with the two CT imaging operations which is the normal number of rounds. Then, the sinogram is corrected using the sinogram obtained by the additional CT imaging operation (S1102).

For example, in FIG. 7, if the variation period of the first sinogram 70a and the variation period of the second sinogram 70b are overlapped at the angle of the period b, the period b is supplemented using the additional sinogram obtained by the additional CT imaging. Alternatively, for the data other than the variation period, the sinogram obtained by the two CT imaging operations, which is the normal number of rounds, and the additional sinogram may be averaged. With such a configuration, for example, further improvement of the image SN ratio can be expected.

When the data variation caused by respiration is removed by the additional round of CT imaging in this manner, it is judged in the flowchart of FIG. 11 that there is no data variation caused by respiration (S1103), and the tomographic image is formed based on the corrected sinogram obtained by the two CT imaging operations and the additional CT imaging operation (S1105). Alternatively, it is also possible to employ a configuration where, when the data variation caused by respiration is not removed by the additional round of CT imaging, an additional CT imaging operation is further executed in step S1104.

Referring again to FIG. 1, after the CT imaging for a number of operations necessary for generation of the tomographic image is completed for one imaging site, the operation controller 44 drives the slide mechanism, to move the subject in the direction of the rotational axis. Then, the respiration synchronization imaging is executed in a process similar to the above for a new imaging site. Specifically, the first CT imaging operation is executed, and the body characteristic is calculated and the sinogram is generated based on the projection data obtained by the CT imaging operation. Then, while the timing is controlled based on the calculated body movement characteristic, the second CT imaging operation is executed to generate the second sinogram, and an additional sinogram is generated as necessary. In other words, according to the present embodiment, every time the imaging site is updated, the body movement characteristic is newly calculated. As a result, even when the body movement characteristic such as the respiration period changes as the time elapses, it is possible to follow the change of the body movement characteristic.

As is clear from the above description, in the present embodiment, because the influence of the body movement is reduced during the image formation process, diagnosis with higher reliability can be enabled. In the above description, in order to simplify the description, the variation period U and the respiration period T are assumed to be in the relationship of $U<T/2$, but the present embodiment can be applied in cases where $U \geq T/2$. In the case where $U \geq T/2$, two or three CT imaging operations may be executed as the normal number of rounds while shifting the phase of the respiration from each other. The corrected sinogram then may be generated in which the data variation caused by respiration is removed or reduced, based on three or more obtained sinograms. When the third CT imaging operation is executed, the body movement characteristic is re-calculated based on the projection data obtained in the second CT imaging operation, and the start timing of the third CT imaging operation is controlled based on the re-calculated body movement characteristic. Similarly, for the subsequent CT imaging operation, the body movement characteristic is re-calculated based on the projection data obtained in the Nth CT imaging operation, and the start timing of the (N+1)th CT imaging operation is controlled based on the re-calculated body movement characteristic. In other words, the start timing of the second CT imaging operation and later executed for one imaging site is controlled based on the body movement characteristic calculated based on the projection data obtained by the CT imaging operation which is executed immediately before the current CT imaging. In this manner, even when the respiration period or the like varies as time elapses, an accurate respiration period or the like can be always obtained.

A preferred embodiment of the present invention has been described. The above-described preferred embodiment, however, is merely exemplary in every aspect, and does not limit the scope of the present invention. The present invention includes various modifications within the scope and spirit of the present invention.

EXPLANATION OF REFERENCE NUMERALS

10 MEASUREMENT UNIT; 12 CALCULATION CONTROLLER; 16 BODY; 18 GANTRY; 20 OPERATION

PANEL; 24 CONTAINER; 26 ARM; 30 PROCESSOR; 32 DISPLAY; 34 STORAGE DEVICE; 36 KEYBOARD; 38 MOUSE; 40 PRINTER; 42 COMMUNICATION UNIT; 44 OPERATION CONTROLLER; 46 BODY MOVEMENT CHARACTERISTIC CALCULATING UNIT; 47 SINOGRAM GENERATOR; 48 SINOGRAM CORRECTING UNIT; 49 TOMOGRAPHIC IMAGE GENERATOR; 52 X-RAY GENERATOR; 54 COLLIMATOR; 56 X-RAY BEAM; 58 EFFECTIVE FIELD OF VIEW; 60 X-RAY DETECTOR; 61 X-RAY DETECTING ELEMENT; 62 DISPLACEMENT MECHANISM; 66 GANTRY ROTATING MECHANISM; 68 SLIDE MECHANISM; 70 SINOGRAM; 100 SUBJECT

The invention claimed is:

1. An X-ray image formation device comprising:
   an X-ray measurement unit which obtains X-ray detection data by radiating X-rays to a subject in a circular moving manner to circle around the subject and detecting the X-rays;
   a body movement measurement unit which obtains body movement period data related to a periodic body movement of the subject;
   a circling controller which controls the circling of the circular moving manner of the radiating X-rays by the X-ray measurement unit based on the body movement period data such that a periodic body movement component in the X-ray detection data obtained for each round of circling of the circular moving X-rays is shifted in the X-ray detection data obtained by the X-ray measurement unit for a plurality of rounds of circling of the circular moving X-rays; and
   an image formation unit which forms image data of the subject while correcting the periodic body movement component based on the X-ray detection data obtained by the plurality of rounds of circling, wherein
   the circling controller executes a control to add another round of circling of the circular moving X-rays when the periodic body movement components overlap with each other to cause a component to remain in the X-ray detection data obtained by a predetermined number of rounds of circling set in advance.

2. The X-ray image formation device according to claim 1, wherein
   the body movement measurement unit obtains the body movement period data based on a body movement periodic component related to a periodic body movement of the subject included in the X-ray detection data.

3. The X-ray image formation device according to claim 1, wherein
   the body movement measurement unit extracts the periodic body movement component from a sinogram correlating an angle of circling and projection data of X-rays for each round of circling.

4. The X-ray image formation device according to claim 3, wherein
   the circling controller controls the circling of the X-rays by the X-ray measurement unit such that the periodic body movement component appearing in the sinogram obtained for each round of circling does not overlap on the same angle in the sinograms for a plurality of rounds of circling.

5. The X-ray image formation device according to claim 4, wherein
   the circling controller determines a start timing of circling of the X-rays based on a period of body movement calculated from the body movement period data such that a phase of the periodic body movement component appearing in the sinogram obtained for each round of circling is shifted in the sinograms for the plurality of rounds of circling.

6. The X-ray image formation device according to claim 5, wherein
   the circling controller executes a control such that, when a periodic body movement component overlapping on the same angle such that the periodic body movement component remains in the sinogram obtained by the predetermined number of rounds of circling, the periodic body movement component is shifted from the angle in the sinogram obtained by adding another round of circling.

7. The X-ray image formation device according to claim 6, wherein
   the image formation unit forms the image data of the subject based on the sinograms obtained by a plurality of rounds of circling while correcting projection data of an angle where the periodic body movement component appears in a sinogram of one round of circling using projection data corresponding to the angle in a sinogram of another round of circling.

8. The X-ray image formation device according to claim 5, wherein
   the image formation unit forms the image data of the subject based on the sinograms obtained by a plurality of rounds of circling while correcting projection data of an angle where the periodic body movement component appears in a sinogram of one round of circling using projection data corresponding to the angle in a sinogram of another round of circling.

9. The X-ray image formation device according to claim 4, wherein
   the image formation unit forms the image data of the subject based on the sinograms obtained by a plurality of rounds of circling while correcting projection data of an angle where the periodic body movement component appears in a sinogram of one round of circling using projection data corresponding to the angle in a sinogram of another round of circling.

10. The X-ray image formation device according to claim 3, wherein
    the image formation unit forms the image data of the subject based on the sinograms obtained by a plurality of rounds of circling while correcting projection data of an angle where the periodic body movement component appears in a sinogram of one round of circling using projection data corresponding to the angle in a sinogram of another round of circling.

11. A non-transitory computer-readable medium storing a program thereon for controlling an X-ray measurement unit which obtains X-ray detection data by radiating X-rays to a subject in a circular moving manner to circle around the subject and detecting the X-rays, the program, when executed by a computer, causing the computer to realize:
    a body movement measurement function in which body movement period data related to a periodic body movement of the subject is obtained; and
    a circling control function in which the circling of the circular moving manner of the radiating X-rays by the X-ray measurement unit is controlled based on the body movement period data such that a periodic body movement component in the X-ray detection data obtained for each round of circling of the circular moving X-rays is shifted in the X-ray detection data obtained by the X-ray measurement unit for a plurality of rounds of circling of the circular moving X-rays, and performing additional round of circling of the circular moving X-rays when the periodic body movement components overlap with each other to cause a component to remain in the X-ray detection data obtained by a predetermined number of rounds of circling which is set in advance.

* * * * *